United States Patent
Pereira et al.

(10) Patent No.: US 6,902,586 B2
(45) Date of Patent: Jun. 7, 2005

(54) PHOSPHATE DYE PRECURSORS AND USE THEREOF FOR DYEING KERATIN FIBERS

(75) Inventors: Rui Pereira, La Riche (FR); Richard Martin, Rochecorbon (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/186,682

(22) Filed: Jul. 2, 2002

(65) Prior Publication Data

US 2003/0037387 A1 Feb. 27, 2003

(30) Foreign Application Priority Data

Jul. 6, 2001 (FR) ............................................. 01 09017

(51) Int. Cl.$^7$ ................................................. A61K 7/06
(52) U.S. Cl. ..................... 8/401; 8/405; 8/406; 8/410; 8/411; 8/421; 8/428; 8/437; 8/451; 548/412
(58) Field of Search ........................... 8/401, 405, 406, 8/410, 411, 421, 428, 437, 451; 548/412

(56) References Cited

U.S. PATENT DOCUMENTS

| 3,002,893 A | | 10/1961 | Babson et al. |
| 5,073,174 A | | 12/1991 | Vayssie et al. |
| 5,589,328 A | | 12/1996 | Mahant |
| 5,645,609 A | * | 7/1997 | Andrean et al. ............... 8/405 |
| 5,965,114 A | | 10/1999 | Braun et al. |

FOREIGN PATENT DOCUMENTS

| FR | 2 779 951 | | 12/1999 | |
| GB | 1128371 | | 9/1968 | |
| JP | 56o73179 A | * | 11/1979 | ............. D06P/1/12 |

* cited by examiner

*Primary Examiner*—Mark Kopec
*Assistant Examiner*—Eisa Elhilo
(74) *Attorney, Agent, or Firm*—Nixon & Vanderhye P.C.

(57) ABSTRACT

The present invention relates to the use for dyeing keratin fibers, in particular human keratin fibers such as the hair, of a dye precursor bearing at least one phosphate substituent of formula —O—PO(OH)$_2$, in the presence of at least one acid or alkaline phosphatase.

24 Claims, No Drawings

PHOSPHATE DYE PRECURSORS AND USE THEREOF FOR DYEING KERATIN FIBERS

The present invention relates to the use of phosphate dye precursors for dyeing keratin fibres, and in particular human keratin fibres, to cosmetic dye compositions and to the process for dyeing keratin fibres using them.

It is known practice to dye keratin fibres, and in particular the hair, with dye compositions containing oxidation dye precursors, generally known as "oxidation bases", in particular ortho- or para-phenylenediamines, ortho- or para-aminophenols and heterocyclic bases.

Oxidation dye precursors are compounds that are initially uncoloured or only slightly coloured, and that develop their dyeing power on the hair in the presence of an oxidizing agent. The oxidizing agent used is generally hydrogen peroxide. The formation of coloured compounds results either from the coupling of the oxidation bases with themselves, or from the coupling of the oxidation bases with coloration modifiers, or "couplers", which are generally present in dye compositions used for oxidation dyeing and which are represented more particularly by meta-phenylenediamines, meta-aminophenols, meta-diphenols and certain heterocyclic compounds.

These well-known prior art processes are not entirely satisfactory and it is consequently sought to develop coloration systems, in particular for the hair, using novel dye precursors.

There also exists hydroxylated compounds such as indoxyl, which form a coloured pigment on oxidation. In the case of indoxyl, it forms indigo, the blue-coloured pigment known for thousands of years for its use in dyeing textiles and colouring the hair.

However, this indigo precursor is not stable in solution. It is thus unsuitable for preparing dye compositions. Furthermore, indigo is a water-insoluble compound, which results in many problems, for instance difficulty in penetrating the hair, poor uniformity of dyeing, the appearance of pigment aggregates, and instability of the compositions containing this pigment.

U.S. Pat. No. 5,965,114 from Braun et al. uses an indoxyl derivative containing a DL, D or L-aldopyranose group or a DL, D or L-ketopyranose group. This derivative is hydrolysed to indoxyl at the time of use in order to obtain blue or purple colorations. The drawback associated with products of this type is that the enzymes used cannot be used at very alkaline pHs, and the dyeing results obtained do not have very good covering power.

The Applicant has just discovered that it is possible to obtain on keratin fibres dyes with good covering power, in intense and varied shades, using dye precursors bearing a phosphate substituent of formula $-O-PO(OH)_2$, in the presence of an acid or alkaline phosphatase. These precursors have the advantage of being water-soluble and stable. In the presence of an acid or alkaline phosphatase, these precursors form a dye that is capable of dyeing keratin fibres.

The colorations obtained moreover show good resistance to perspiration, to light and to shampooing.

One subject of the invention is thus the use, for dyeing keratin fibres, of phosphate oxidation dye precursors, in the presence of at least one acid or alkaline phosphatase.

Another subject consists of the dye compositions using them.

A subject of the invention is also a process for dyeing keratin fibres using these dyes.

Other subjects of the invention will become apparent on reading the description and the examples that follow.

The oxidation dye precursors used for dyeing keratin fibres, and more particularly human keratin fibres such as the hair, are dye precursors, i.e. compounds that can form a dye on oxidation, these precursors bearing at least one phosphate substituent of formula $-O-PO(OH)_2$.

These compounds are in particular aromatic compounds containing one or more fused rings, these rings possibly being 5- or 6-membered carbocycles or heterocycles containing one or more hetero atoms chosen from oxygen and nitrogen, and substituted with at least one phosphate group.

The phosphate dye precursors used in accordance with the invention are preferably chosen from benzene, naphthalene, indole or indolene derivatives optionally substituted with one or more halogen atoms or with one or more carboxyl, alkoxy, aryloxy, nitro, cyano, carbamyl, acylamino, amino, alkylamino, sulphonamido or hydroxyalkyl groups.

The halogen atom(s) is (are) chosen from bromine, chlorine, fluorine and iodine.

The alkoxy, acylamino, alkylamino and hydroxyalkyl groups preferably contain from 1 to 4 carbon atoms.

The compounds that may be used in oxidation dyeing according to the invention are especially: 3-indoxyl phosphate, 4-chloro-3-indoxyl phosphate, 6-chloro-3-indoxyl phosphate, 5-bromo-6-chloro-3-indoxyl phosphate, 5-bromo-4-chloro-3-indoxyl phosphate, 6-flouoro-3-indoxyl phosphate, 5-iodo-3-indoxyl phosphate, N-methyl-3-indoxyl phosphate, α-naphtyl phosphate of formula

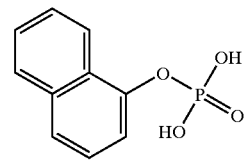

naphthol AS-TR phosphate of formula

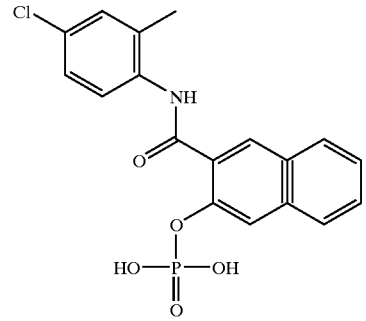

β-naphthyl phosphate of formula

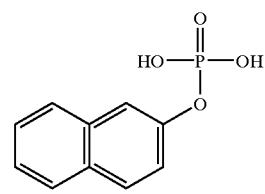

naphthol AS-BI phosphate of formula
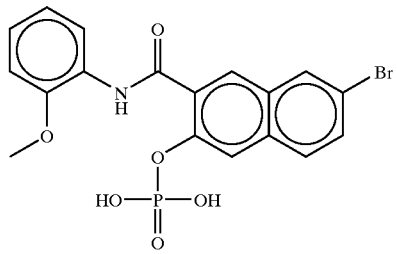
4-methylumbelliferyl phosphate of formula
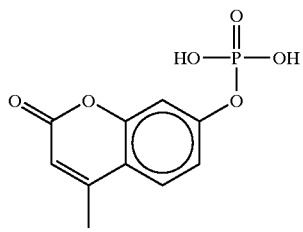
naphthol AS phosphate of formula
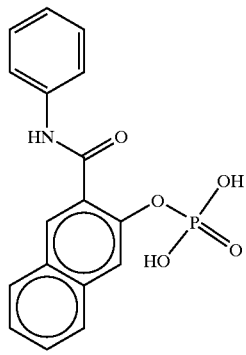
naphthol AS-OL phosphate of formula
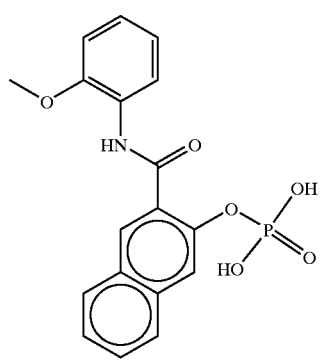
naphthol AS-KB phosphate of formula
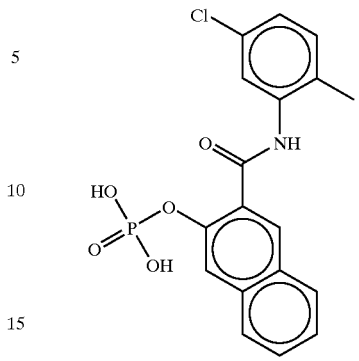
the compound of formula
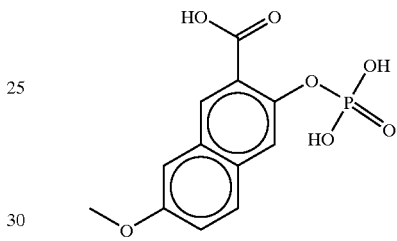
the compound of formula
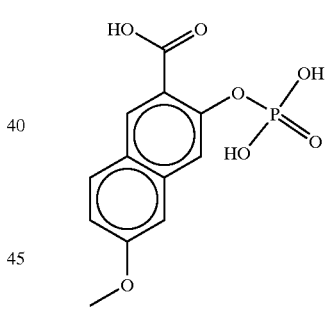
the compound of formula
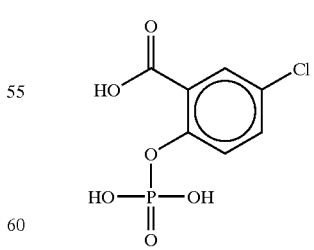
The dye precursor is preferably chosen from the compounds of formula (I):

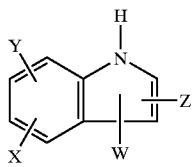

in which
- W, X and Y each independently represent a hydrogen atom, a halogen atom or a hydroxyl, carboxyl or alkoxy group containing from 1 to 4 carbon atoms,
- Z represents a phosphate group —O—PO(OH)$_2$, the said group Z possibly being borne by any carbon atom of either of the two rings.

According to one particular embodiment, the substituent Z is borne by the carbon C-3.

These compounds are used in combination with at least one acid or alkaline phosphatase.

Phosphatase is an enzyme capable of converting a phosphoric monoester R—O—PO(OH)$_2$ into alcohol and orthophosphate. Such an enzyme is also known under the name acid or alkaline phosphomonoesterase, acid or alkaline glycerophosphatase, or acid or alkaline phosphohydrolase of phosphoric acid monoester.

Alkaline phosphatases are listed under the numbering E.C.3.1.3.1. and acid phosphatases are listed under the numbering E.C.3.1.3.2., according to the enzyme nomenclature described in "Enzyme Nomenclature: Recommendations (1992) of the Nomenclature Committee of the International Union of Biochemistry and Molecular Biology" published by Academic Press.

The acid or alkaline phosphatases used in the present invention may be chosen especially from phosphatases extracted from plants, animals, insects or microorganisms, particularly from differentiated or undifferentiated cells, obtained in vivo or in vitro, before or after genetic modification.

One subject of the invention is thus the use for dyeing keratin fibres, and in particular human keratin fibres such as the hair, of a dye precursor bearing at least one phosphate substituent of formula —O—PO(OH)$_2$, with at least one acid or alkaline phosphatase.

For the purposes of the invention, the expression "human keratin fibres" mainly means head hair, other hairs, the eyelashes and the eyebrows, and more particularly head hair.

A subject of the invention is also a composition for dyeing keratin fibres, in particular human keratin fibres such as the hair, characterized in that it comprises, in a medium that is suitable for dyeing, at least one of the dye precursors defined above and at least one acid or alkaline phosphatase.

The pH of the composition may be between 7 and 11 and preferably between 8 and 10.

The compound of formula (I) is preferably present in the composition in proportions of between 0.2% and 10% and even more preferably between 0.5% and 2% of the total weight of the composition.

The alkaline or acid phosphatase may be present in the composition in a concentration of between 50 and 2000 activity units per 100 g of composition, preferbly between 200 and 500 activity units per 100 g of composition, the enzymatic activity being defined as the amount of substrate required to convert 1 µmol of substrate per minute in 50 µmol of diethanolamine at a pH of 9.5 adjusted with NaOH or HCl, at a temperature of 37° C.

The composition may also contain an oxidizing agent. This oxidizing agent may be chosen from the oxidizing agents conventionally used for the oxidation dyeing of keratin fibres, such as hydrogen peroxide, urea peroxide, alkali metal bromates, persalts such as perborates and persulphates, enzymes such as 2-electron oxidoreductases, 4-electron oxidoreductases such as laccases, producing in situ hydrogen peroxides in the presence of atmospheric oxygen, these systems containing, for example, glucose oxidases, choline oxidases, galactose oxidases, uricases and peroxidases, for instance horseradish peroxidase, cytochrome C, chloroperoxidase and microperoxidase.

The dye composition may also contain oxidation bases other than the compounds of formula (I) and chosen, for example, from para-phenylenediamines, bis(phenyl)alkylenediamines, para-aminophenols, ortho-aminophenols, heterocyclic bases, and/or couplers chosen from meta-phenylenediamines, meta-aminophenols, meta-diphenols and heterocyclic couplers.

Among the para-phenylenediamines which can be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxy-ethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyl-para-phenylenediamine, 2-β-acetylaminoethyloxy-para-phenylenediamine and N-(β-methoxyethyl)-para-phenylenediamine, and the addition salts thereof with an acid.

Among the para-phenylenediamines mentioned above, the ones most particularly preferred are para-phenylenediamine (PPD), para-tolylenediamine, 2-isopropyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(βhydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)-ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

Among the pyridine derivatives which may be mentioned more particularly are the compounds described, for example, in patents GB 1 026 978 and GB 1 153 196 such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives which may be mentioned more particularly are the compounds described, for example, in German patent DE 2 359 399 or Japanese patents JP 88-169 571 and JP 91-10659 or patent application WO 96/15765, such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine.

Among the pyrazole derivatives which may be mentioned more particularly are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-hydroxymethylpyrazole, 4,5-diamino-3-hydroxymethyl-1-methylpyrazole, 4,5-diamino-3-hydroxy-methyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylamino-pyrazole and 3,5-diamino-4-(β-hydroxyethyl)amino-1-methylpyrazole, and the addition salts thereof with an acid.

The oxidation base(s) preferably represent(s) from 0.0005% to 12% by weight approximately relative to the total weight of the dye composition, and even more preferably from 0.005% to 6% by weight approximately relative to this weight.

The dye composition in accordance with the invention can also contain one or more additional couplers that may be chosen from the couplers used conventionally in oxidation dyeing and among which mention may be made in particular of meta-phenylenediamines, meta-aminophenols and meta-diphenols and heterocyclic couplers such as, for example, indole derivatives, indoline derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 4-hydroxy-N-methylindole, 2,6-dihydroxy-4-methylpyridine, 1-H-3-methylpyrazol-5-one and 1-phenyl-3-methylpyrazol-5-one, and the addition salts thereof with an acid.

When they are present, these additional couplers preferably represent from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, citrates, succinates, tartrates, lactates and acetates.

The medium which is suitable for dyeing (or the support) generally consists of water or a mixture of water and at least one organic solvent in order to solubilize the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention may be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (II) below:

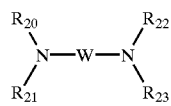

in which W is a propylene residue optionally substituted with a hydroxyl group or a $C_1$–$C_6$ alkyl radical; $R_{20}$, $R_{21}$, $R_{22}$ and $R_{23}$, which may be identical or different, represent a hydrogen atom, a $C_1$–$C_6$ alkyl radical or a $C_1$–$C_6$ hydroxyalkyl radical.

Buffer media may also be used, for example diethanolamine, borate, 2-amino-2-methyl-1-propanol, glycine, trimethylamine, pyrophosphate, methylamine or carbonate.

The dye composition may also contain direct dyes such as azo dyes, anthraquinone dyes and nitrobenzene derivatives or melanin precursors.

The nitrobenzene dyes are, for example, nitrophenyl-enediamines, nitrodiphenylamines, nitroanilines, nitrophenyl ethers or nitrophenols, nitropyridines, anthraquinone dyes, mono- or diazo dyes, triarylmethane dyes, azine dyes, acridine dyes and xanthene dyes, or alternatively metalliferous dyes. The proportion of all these direct addition dyes can range between 0.05% and 10% by weight relative to the total weight of the dye composition.

The said dye composition may also contain any other adjuvants commonly used in the dyeing of keratin materials, and for example surfactants known in the prior art and of anionic, cationic, nonionic, amphoteric or zwitterionic type or mixtures thereof, thickeners, antioxidants, fragrances, sequestering agents, dispersants, conditioners, preserving agents, opacifiers, etc.

The composition applied to the hair may be in various forms, such as in the form of liquid, cream or gel or in any other form that is suitable for dyeing keratin fibres. In particular, it may be packaged under pressure in an aerosol can in the presence of a propellant and form a mousse.

Needless to say, a person skilled in the art will take care to select the optional additional compound(s) mentioned above, such that the advantageous properties intrinsically associated with the dye composition according to the invention are not, or are not substantially, adversely affected by the envisaged addition(s).

A subject of the present invention is also a process for dyeing keratin fibres, and in particular human keratin fibres such as the hair, which consists in applying one of the compositions defined above to the keratin materials.

One of the subjects of the present invention is also a process for dyeing keratin fibres, in particular human keratin fibres such as the hair, which consists in applying to the said fibres at least one component (A) consisting of a composition containing, in a medium that is suitable for dyeing, at least one of the phosphate dye precursors defined above, and at least one component (B) consisting of a composition containing, in a medium that is suitable for dyeing, at least one alkaline or acid phosphatase, component (B) being extemporaneously mixed with component (A) just before use or applied sequentially before, after or simultaneously with component (A). An oxidizing agent may be incorporated into component (B).

According to one process of the invention, components (A) and (B) are mixed together just before use. The mixture obtained is then applied immediately to the keratin fibres. Next, the mixture is left to act for 1 to 60 minutes, preferably for 1 to 30 minutes. The keratin fibres are then rinsed, washed with shampoo, rinsed again and then dried.

It is also possible to apply components (A) and (B) successively to the keratin fibres, the order of application being irrelevant, to leave them to act for 1 to 60 minutes and preferably for 1 to 30 minutes, to perform an optional rinsing with water between each application, and then to rinse, wash with shampoo, rinse again and then dry the said keratin fibres.

A subject of the present invention is also an agent for dyeing keratin fibres, and in particular human keratin fibres such as the hair, comprising components (A) and (B) defined above, in separate form, components (A) and (B) being intended either to be mixed just before use or to be applied successively to the fibres to be treated.

An oxidizing agent may be incorporated into component (B).

A subject of the present invention is also a multi-compartment device or "dyeing kit", which comprises at least two compartments, the first of which contains component (A) and the second of which contains component (B). An oxidizing agent may be incorporated into component (B).

The multi-compartment device or "dyeing kit" defined above can comprise three compartments, the first containing component (A), the second containing component (B), at least one of the components (A) and (B) being in the form of an anhydrous composition, and the third containing an aqueous medium that is suitable for dyeing, the said medium being intended to be mixed before use with at least one of the components (A) and (B).

The examples that follow, which are in no way limiting, are intended to illustrate the invention.

EXAMPLES

The phosphatase used in the following examples is *Escherichia coli* K12 phosphatase, sold by the company Sigma.

Example 1

The dye composition below is prepared just before use:

| | |
|---|---|
| 3-indoxyl phosphate | 0.5 g |
| alkaline phosphatase | 400 units |
| 0.1 M buffer of diethanolamine in water at pH 9.6 | 94.5 g |

The above composition is applied to locks of natural grey hair containing 90% white hairs and is left in place for 30 minutes. After rinsing out with running water and drying, the hair is dyed a dark blue indigo shade.

Example 2

The dye composition below is prepared just before use:

| | |
|---|---|
| 3-indoxyl phosphate | 0.5 g |
| alkaline phosphatase | 400 units |
| 0.1 M buffer of diethanolamine in water at pH 9.6 | 94.5 g |

The above composition is applied to locks of natural grey hair containing 90% white hairs and is left in place for 30 minutes. After rinsing out with running water and drying, the hair is dyed a magenta shade.

Example 3

The dye composition below is prepared just before use:

| | |
|---|---|
| 3-indoxyl phosphate | 0.5 g |
| alkaline phosphatase | 400 units |
| 0.1 M buffer of diethanolamine in water at pH 9.6 | 94.5 g |

The above composition is applied to locks of natural grey hair containing 90% white hairs and is left in place for 30 minutes. After rinsing out with running water and drying, the hair is dyed a blue shade.

Example 4

Dye compositions are prepared by carrying out the following steps:

Step 1

The following compounds are added in the amounts indicated:

| Compound | Final concentration |
| --- | --- |
| diethanolamine buffer | 0.106 M |
| phosphated compound | 1 mM |
| base or coupler | 1 mM |
| alkaline phosphatase | 2500 U/100 g |

This composition is applied to locks of natural grey hair (90% white hairs).

The locks are then incubated at 37° C. for 30 minutes.

Step 2

4-Volumes aqueous hydrogen peroxide solution (1.2% by weight) is then applied. This solution is left in place for 15 minutes and the hair is then washed, rinsed and dried.

The results obtained with three phosphate compounds are given in the table below.

| Phosphate compound | base or coupler | colour |
| --- | --- | --- |
| α-Naphthyl phosphate | 4-aminophenol | salmon |
|  | 5-methylpyrazolo[1,5-a]-pyrimidine-3,7-diamine | dark pink |
|  | PPD | purple |
|  | 4,5-diamino-1-ethyl-3-methylpyrazole | purple |
|  | 5-amino-2-methylphenol | purple |
| Naphthol AS-TR phosphate | 5-methylpyrazolo[1,5-a]-pyrimidine-3,7-diamine | cyan blue |
| β-Naphthyl phosphate | 5-methylpyrazolo[1,5-a]-pyrimidine-3,7-diamine | purple |

What is claimed is:

1. A method or dying keratin fibres comprising contacting said fibres with a dye precursor bearing at least one phosphate substituent of formula —O—PO(OH)$_2$, in the presence of at least one acid or alkaline phosphatase.

2. The method of claim 1, characterized in that the dye precursor is an aromatic compound containing one or more fused rings, these rings possibly being 5- or 6-membered carbocyles or heterocycles containing one or more hetero atoms chosen from oxygen and nitrogen, and substituted with at least one phosphate group.

3. The method of claim 1, characterized in that the dye precursor is chosen from the compounds of formula (I):

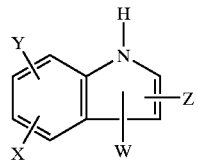

in which

W, X and V each independently represent a hydrogen atom, a halogen atom or a hydroxyl, carboxyl or alkoxy group containing from 1 to 4 carbon atoms, Z represents a phosphate group —O—PO(OH)$_2$, the said group Z possibly being borne by any carbon atom of either of the two rings.

4. The method of claim 3, characterized in that the substituent Z is borne by the carbon C-3.

5. The method of claim 3, characterized in that the compound of formula (I) is chosen from 3-indoxyl phosphate, 4-chloro-3-indoxyl phosphate, 6-chloro-3-indoxyl phosphate, 5-bromo-6-chloro-3-indoxyl phosphate, 5-bromo-4-chloro-3-indoxyl phosphate, 6-fluoro-3-indoxyl phosphate, 5-iodo-3-indoxyl phosphate and N-methyl-3-indoxyl phosphate.

6. The method of claim 1, characterized in that the acid or alkaline phosphatase is extracted from plants, animals, insects or microorganisms.

7. A composition for dyeing keratin fibres, characterized in that it comprises, in a medium that is suitable for dyeing, at least one dye precursor defined in claim 1, and at least one acid or alkaline phosphatase.

8. The dye composition according to claim 7, characterized in that it has a pH of between 7 and 11.

9. The composition according to claim 7, characterized in that the dye precursor is present in proportions of between 0.2% and 10% relative to the total weight of the composition.

10. The composition according to claim 7, characterized in that the alkaline or acid phosphatase is present in a concentration of between 50 and 2000 activity units per 100 g of composition.

11. The composition according to claim 7, characterized in that it also contains an oxidizing agent.

12. The composition according to claim 7, characterized in that it also contains oxidation bases other than the dye precursor and chosen from para-phenylenediamines, bis (phenyl) alkylenediamines, para-aminophenols, ortho-amino-phenols, heterocyclic bases and/or couplers chosen from meta-phenylenediamines, meta-aminophenols, meta-diphenols and heterocyclic couplers.

13. The composition according to claim 7, characterized in that it also contains direct dyes chosen from azo dyes, anthraquinone dyes, nitrobenzene derivatives and melanin precursors.

14. The composition according to claim 7, characterized in that the medium that is suitable for dyeing is a medium containing water or a mixture of water and at least one organic solvent chosen from alcohols, glycols and glycol ethers, the solvents being present in proportions of between 1% and 25% relative to the total weight of the composition.

15. A process for dyeing keratin fibres, characterized in that it consists in applying to the said fibres the composition according to claim 7.

16. A process for dyeing keratin fibres, characterized in that it consists in applying to the said fibres at least one component (A) consisting of a composition containing, in a medium that is suitable for dyeing, at least one of the phosphate dye precursors defined in claim 1, and at least one component (B) consisting of a composition containing, in a medium that is suitable for dyeing, at least one alkaline or acid phosphatase, component (B) being extemporaneously mixed with component (A) just before use or applied sequentially before, after or simultaneously with component (A).

17. The process according to claim 16, characterized in that it comprises the steps consisting In mixing components (A) and (B) just before use, immediately applying the mixture obtained to the keratin fibres, leaving it to act for 1 to 60 minutes and preferably for 1 to 30 minutes, rinsing, washing with shampoo, rinsing again and then drying the said keratin fibres.

18. The process according to claim 16, characterized in that it comprises the steps consisting in successively applying to the keratin fibres components (A) and (B), the order of application being irrelevant, leaving them to act for 1 to 60 minutes and preferably for 1 to 30 minutes, optionally rinsing with water between each application, rinsing, washing with shampoo, rinsing again and then drying the said keratin fibres.

19. An agent for dyeing keratin fibres, and characterized in that it comprises components (A) and (B) as defined in claim 16, in separate form, components (A) and (B) being intended either to be mixed just before use or to be applied successively to the fibres to be treated.

20. A multi-compartment device or "dyeing kit", characterized in that it comprises at least two compartments, the first of which contains component (A) as defined in claim 16, and the second of which contains component (B) as defined in claim 16.

21. The device according to claim 20, characterized in that it comprises three compartments, the first containing component (A), the second containing component (B), at least one of the components (A) and (B) being in the form of an anhydrous composition, the third compartment containing an aqueous medium that is suitable for dyeing, the said medium being intended to be mixed before use with at least one of the components (A) and (B).

22. The dye composition according to claim 7, characterized in that it has a pH of between 8 and 10.

23. The composition according to claim 7, characterized in that the dye precursor is present in proportions of between 0.5% and 2% relative to the total weight of the composition.

24. The composition according to claim 7, characterized in that the alkaline or acid phosphatase is present in a concentration of between 200 and 500 activity units per 100 g of composition.

* * * * *